(12) United States Patent
DiPiero et al.

(10) Patent No.: US 8,706,524 B2
(45) Date of Patent: *Apr. 22, 2014

(54) HEALTH PLAN MANAGEMENT METHOD AND APPARATUS

(75) Inventors: Albert R. DiPiero, Portland, OR (US); David G. Sanders, Portland, OR (US)

(73) Assignee: TriZetto Corporation, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/535,549

(22) Filed: Jun. 28, 2012

(65) Prior Publication Data

US 2012/0271776 A1    Oct. 25, 2012

Related U.S. Application Data

(60) Continuation of application No. 12/576,985, filed on Oct. 9, 2009, now Pat. No. 8,214,230, and a division of application No. 09/990,123, filed on Nov. 21, 2001, now Pat. No. 7,624,026.

(60) Provisional application No. 60/252,518, filed on Nov. 21, 2000.

(51) Int. Cl.
*G06Q 10/00*    (2012.01)

(52) U.S. Cl.
USPC ........ 705/2; 705/4; 705/35; 705/39; 705/322; 235/379

(58) Field of Classification Search
USPC ............................. 705/2, 322, 35, 4; 235/379
See application file for complete search history.

(56) References Cited

U.S. PATENT DOCUMENTS

| | | |
|---|---|---|
| 4,491,725 A | 1/1985 | Pritchard |
| 4,858,121 A | 8/1989 | Barber et al. |
| 4,916,611 A | 4/1990 | Doyle, Jr. et al. |

(Continued)

FOREIGN PATENT DOCUMENTS

| | | | |
|---|---|---|---|
| DE | 19641357 | 9/1998 | ............ G06F 17/60 |
| JP | 11242270 | 9/1999 | ............ G03B 15/05 |

(Continued)

OTHER PUBLICATIONS

"National Health Plan Identifier, The Establishment of a Standard for a National Health Plan Identifier Issue Paper" [online], Mar. 11, 1998 [retrieved on Dec. 14, 2010], 13 pp., Retrieved from the Internet: http://www.payorid.com/Medicare/HIPAA.htm.

(Continued)

*Primary Examiner* — Vanel Frenel
(74) *Attorney, Agent, or Firm* — Dawn-Marie Bey; Bey & Cotropia PLLC

(57) ABSTRACT

Techniques and apparatus for managing contributions to an accruable health spending account in an employer-sponsored plan offering a member an employer-funded defined contribution, at least one insurance premium option and the ability to specify an allocation of the defined contribution for payment of option premiums and in turn, a directed contribution amount designated to such accruable account are disclosed. The accruable account may be used to reimburse the member for qualified medical expenses, and the member may pay any premium shortfall using a tax-advantaged process such as a premium only payment plan. Also disclosed are techniques and apparatus directed to presenting member-specific out-of-pocket expenses for a selected procedure offered by at least one health-care provider.

18 Claims, 15 Drawing Sheets

(56) References Cited

U.S. PATENT DOCUMENTS

| | | |
|---|---|---|
| 5,134,564 A | 7/1992 | Dunn et al. |
| 5,136,502 A | 8/1992 | Van |
| 5,235,507 A | 8/1993 | Sackler et al. |
| 5,253,164 A | 10/1993 | Holloway et al. |
| 5,301,105 A | 4/1994 | Cummings, Jr. |
| 5,324,077 A | 6/1994 | Kessler et al. |
| 5,333,317 A | 7/1994 | Dann |
| 5,359,509 A | 10/1994 | Little et al. |
| 5,471,382 A | 11/1995 | Tallman et al. |
| 5,517,405 A | 5/1996 | McAndrew et al. |
| 5,544,044 A | 8/1996 | Leatherman |
| 5,583,760 A | 12/1996 | Klesse |
| 5,644,778 A | 7/1997 | Burks et al. |
| 5,692,501 A | 12/1997 | Minturn |
| 5,704,044 A | 12/1997 | Tarter et al. |
| 5,724,379 A | 3/1998 | Perkins et al. |
| 5,802,500 A | 9/1998 | Ryan et al. |
| 5,832,447 A | 11/1998 | Rieker et al. |
| 5,845,254 A | 12/1998 | Lockwood et al. |
| 5,879,163 A | 3/1999 | Brown et al. |
| 5,884,275 A | 3/1999 | Peterson et al. |
| 5,915,241 A | 6/1999 | Giannini |
| 5,930,759 A | 7/1999 | Moore et al. |
| 5,950,169 A | 9/1999 | Borghesi et al. |
| 5,970,463 A | 10/1999 | Cave et al. |
| 5,976,082 A | 11/1999 | Wong et al. |
| 5,991,733 A | 11/1999 | Aleia et al. |
| 6,012,035 A | 1/2000 | Freeman, Jr. et al. |
| 6,014,632 A | 1/2000 | Gamble et al. |
| 6,044,352 A | 3/2000 | Deavers |
| 6,064,983 A | 5/2000 | Koehler |
| 6,067,522 A | 5/2000 | Warady et al. |
| 6,088,677 A | 7/2000 | Spurgeon |
| 6,108,641 A | 8/2000 | Kenna et al. |
| 6,112,183 A | 8/2000 | Swanson et al. |
| 6,125,354 A | 9/2000 | MacFarlane et al. |
| 6,151,586 A | 11/2000 | Brown |
| 6,163,770 A | 12/2000 | Gamble et al. |
| 6,208,973 B1 | 3/2001 | Boyer et al. |
| 6,235,176 B1 | 5/2001 | Schoen et al. |
| 6,253,186 B1 | 6/2001 | Pendleton, Jr. |
| 6,283,761 B1 | 9/2001 | Joao |
| 6,324,516 B1 | 11/2001 | Shults et al. |
| 6,341,265 B1 | 1/2002 | Provost et al. |
| 6,343,271 B1 | 1/2002 | Peterson et al. |
| 6,343,310 B1 | 1/2002 | DiRienzo |
| 6,401,079 B1 | 6/2002 | Kahn et al. |
| 6,434,531 B1 | 8/2002 | Lancelot et al. |
| 6,453,297 B1 | 9/2002 | Burks et al. |
| 6,587,829 B1 | 7/2003 | Camarda et al. |
| 6,735,569 B1 | 5/2004 | Wizig |
| 6,792,410 B1 | 9/2004 | Donovan et al. |
| 6,915,265 B1 | 7/2005 | Johnson |
| 7,016,856 B1 | 3/2006 | Wiggins |
| 7,107,239 B2 | 9/2006 | Graff |
| 7,194,416 B1 | 3/2007 | Provost et al. |
| 7,344,496 B2 | 3/2008 | Iliff |
| 7,464,040 B2 | 12/2008 | Joao |
| 7,774,252 B2 | 8/2010 | Seare et al. |
| 2001/0034618 A1 | 10/2001 | Kessler et al. |
| 2001/0037214 A1 | 11/2001 | Raskin et al. |
| 2001/0037223 A1 | 11/2001 | Beery et al. |
| 2001/0051906 A1 | 12/2001 | Esposito |
| 2002/0010597 A1 | 1/2002 | Meyer et al. |
| 2002/0019754 A1 | 2/2002 | Peterson et al. |
| 2002/0049617 A1 | 4/2002 | Lencki et al. |
| 2002/0069085 A1 | 6/2002 | Engel et al. |
| 2002/0077869 A1 | 6/2002 | Doyle et al. |
| 2002/0095316 A1 | 7/2002 | Toan et al. |
| 2002/0138304 A1 | 9/2002 | Fontanesi |
| 2002/0149616 A1 | 10/2002 | Gross et al. |
| 2002/0152097 A1 | 10/2002 | Javors |
| 2002/0169701 A1 | 11/2002 | Tarbox et al. |
| 2002/0184148 A1 | 12/2002 | Kahn et al. |
| 2003/0009355 A1 | 1/2003 | Gupta |
| 2003/0046116 A1 | 3/2003 | Horowitz et al. |
| 2004/0064386 A1 | 4/2004 | Goguen et al. .......... 705/34 |
| 2005/0033609 A1 | 2/2005 | Yang |
| 2005/0086075 A1 | 4/2005 | Kachler et al. |
| 2005/0108067 A1 | 5/2005 | Chapman et al. |
| 2005/0187797 A1 | 8/2005 | Johnson |
| 2005/0247777 A1 | 11/2005 | Pitroda |
| 2006/0064332 A1 | 3/2006 | Schoenbaum et al. |
| 2007/0203834 A1 | 8/2007 | Field |
| 2010/0235197 A1 | 9/2010 | Dang |

FOREIGN PATENT DOCUMENTS

| | | | |
|---|---|---|---|
| WO | WO 84/01448 | 4/1984 | |
| WO | WO 91/15817 | 10/1991 | ........... G06F 19/00 |
| WO | WO 95/03569 | 2/1995 | ........... G06Q 40/00 |
| WO | WO 95/12857 | 5/1995 | ........... G06Q 17/60 |
| WO | WO 99/22330 | 5/1999 | ........... G06F 19/00 |
| WO | WO 99/44111 | 9/1999 | ........... G06Q 20/00 |
| WO | WO 00/03343 | 1/2000 | ........... G06F 1/00 |
| WO | WO 00/66367 | 11/2000 | ........... B42D 1/10 |

OTHER PUBLICATIONS

Kirby, William H., Jr., "Computer-Based Applications for Providers, Consumers and Insurers in Health Care Services and Education," *IEEE*, pp. 236-242, 1982.

North Carolina, Industrial Commission, Memorandum, "New Mandatory Medical Billing and Reimbursement Procedures," 2 pp., Nov. 30, 1999.

DownSeeker Scripts, "Free Download MedLink Script," 2 pp., Aug. 29, 1999.

The Free Library, "HNC Insurance Solutions Introduces Autoadvisor, the First Integrated Medical Repricing Software With Managed Care Component for the Auto Medical Claims Market" [online], *Business Wire*, Sep. 2, 1998 [retrieved on Dec. 14, 2010], 4 pp., Retrieved from the Internet: http://www.thefreelibrary.com/HNC+Insurance+Sol . . . .

Selby, Dayton W. and Federico, Robert J., "The Effects of Physicians' Computer Applications on Health Insurance Claims and Reimbursements," *IEEE*, pp. 746-751, 1979.

Miller, Lawrence G., "Reducing Health Care Costs Using Claims Adjudication Software" [online], *Physician Executive*, May 1, 1993 [retrieved on Dec. 14, 2010], 4 pp., Retrieved from the Internet: http://www.thefreelibrary.com/Reducing+health+ca . . . .

Waterhouse, Rosie, "Medical Tests for New Benefit 'Unfair': Over-Reliance on Health Evidence Attacked" [online], The Independent, Feb. 17, 1994 [retrieved on Dec. 20, 2010], 1 p., Retrieved from the Internet: http://www.independent.co.uk/news/uk/politics/medical-tests-for-new-benefit-unfair-overreliance-on-healt . . . .

Gustafson, Bobette M., "Preparing for Future Roles as Claims Payers" [online], *Healthcare Financial Management*, Jan. 1, 1996 [retrieved on Dec. 14, 2010[, 3 pp., Retrieved from the Internet: http://www.allbusiness.com/.../538143-1.html.

International Search Report and Written Opinion for Application No. PCT/US2007/070298, dated Jan. 7, 2008, 11 pp.

An EBRI Special Report and Issue Brief No. 124, Mar. 1992, pp. 1-37.

Sourbeer, James N., "Broker World," Praire Village, Mar. 1990, vol. 10, ISS. 3, p. 36. 3 pp., http://proquest.umi.com/pqdweb?index=0&did=998138&SrchMode=1&sid=3&Fmt=2&Vin . . . , Aug. 17, 2006.

IHF Institute for Health Freedom; Update on MSAs, Now Called Health Savings Accounts (HSAs); 3 pages; 1998.

Department of Treasury Internal Revenue Service; Publication 969 (Rev. Apr. 2000); Medical Savings Accounts (MSAs); 10 pages.

Title 26—Internal Revenue Code; posted by http://www.CoreDocuments.com; 10 pages, Jan. 2, 2001.

Health Grades, The Healthcare Quality Experts, Source: www2healthgradws.com.printed Dec. 7, 2001, 64 pages.

(56) References Cited

OTHER PUBLICATIONS

Private Letter Ruling, Internal Revenue Service (I.R.S.), Issue: Feb. 18, 2000 / Nov. 19, 1999, pp. 1-13.
LEXSTAT 26 USC 106; Lexis Law Publishing, 2001, 7 pages.
LEXSTAT IRC sec. 105; Lexis Law Publishing, 2000, 8 pages.
Jacob, Julie A.; Some insurers embracing defined contribution plans; amednews.com; Mar. 12, 2001, 4 pages.
Myhealthbank names two to management team; The Business Journal; Portland; Jun. 2000, 2 pages.

Fig. 4.

EXCHANGE ENGINE OUTPUT

SERVICE: CARDIOLOGY SERVICES
 INITIAL CARDIOLOGY EXAMINATION
TREADMILL
CARDIAC REHABILITATION

SELECTION OF DESIRED SERVICES

|  | STEPHEN WUMPS, MD, FAACP | SUSAN CARLSON, MD, FAACP |
|---|---|---|
| PRICE | $400 | $600 |
| WHAT YOU PAY | $80 | $200 |
| LOCATION | 11 OLD MILL ROAD, PORTLAND, OR 97111  MAP | 244 SNODGRASS PARKWAY, LAKE OSWEGO, OR 98333  MAP |
| RESUME | MD, OHSU, 1978 CARDIOLOGY, UNIV. MARYLAND 1984 CLICK FOR DETAILS | MD, UCSF, 1984 CARDIOLOGY, BAYLOR, 1990 CLICK FOR DETAILS |
| MEMBER REVIEWS | CLICK TO READ | CLICK TO READ |
| PUBLIC RECORDS | 1 LISTING (CLICK TO REVIEW) | 2 LISTINGS (CLICK TO REVIEW) |
| INDEPENDENT RATING | ★ ★ ☆ | ★ ★ ★ |
| WEBSITE | WWW.WUNPSMD.COM | WWW.CARSONHEART.COM |

HEALTH PLAN MANAGEMENT METHOD AND APPARATUS

CROSS-REFERENCE TO RELATED APPLICATIONS

This application claims priority to U.S. application Ser. No. 12/576,985 entitled "Health Plan Management Method and Apparatus" filed Oct. 9, 2009, which claims priority to U.S. application Ser. No. 09/990,123 also entitled "Health Plan Management Method and Apparatus" now U.S. Pat. No. 7,624,026, which claims priority benefit under 35 U.S.C. §119(e)(1) to U.S. Provisional Application No. 60/252,518, filed Nov. 21, 2000, naming Albert R. DiPiero and David G. Sanders as co-inventors, and entitled "Competitive Reimbursement Pricing Engine and Applications for Professional Services Providers, Payers and Consumers," which is incorporated herein fully by reference.

TECHNICAL FIELD

This invention related to health plan management systems and processes, and is particularly concerned with techniques for presenting and managing medical reimbursement and out of pocket expenses for a member of a health plan.

BACKGROUND

Currently, insurance carriers reimburse providers and suppliers of health care or medical services and products based on contracts established between the insurance carrier and the provider/supplier. Today's standard contracts do not permit the providers/suppliers to dynamically change their prices in a way that changes the reimbursement they receive from the insurance carrier. Today providers and suppliers cannot translate differentiation in service, quality or selection into variable reimbursement from insurance carriers because reimbursement is locked in for extended periods and the contracts forbid providers and suppliers from billing the customer of the insurance carrier for more beyond what is agreed to in the contract with the insurance carrier.

Furthermore, currently no method exists for a consumer to determine immediately his out-of-pocket expenses for a range of healthcare products and services across a range of providers and suppliers. Instead, a claim must first be adjudicated, reconciled against the consumers benefits plan, out of pocket maximum, and deductible. Nor can insured customers compare healthcare products and services and judge them based on their individual out of pocket expenses that integrates insured and non-insured payment streams. Likewise, today no method exists for providers and suppliers to change their reimbursement rate for covered services immediately and allow customers to see those changes in terms of their out-of-pocket obligations.

Further still, conventional employee-funded healthcare spending accounts which use pre-tax employee funds in compliance with US law and applicable Internal Revenue Service regulations, commonly known as Flexible Spending Accounts (FSA), fall short of being a truly effective and economically sound vehicle for handling qualified medical expenses (QME) as defined in section 213 of the Internal Revenue code. They do not permit plan participants to act as normal consumers. Instead FSA rules force the participant to predict exactly his healthcare expenses for a 12-month period and punishes the participant, through the use-it-or-loose-it rule, for spending less than predicted so the incentive is to spend all the money before the end of the year. Budgeting too little also hurts the participant, since he/she can no longer gain tax-advantaged payment for qualified medical expenses which exceed the budgeted FSA amount. Moreover, there's a perceived "overcomplexity" of management: the current accounts do not provide for employer or employee a simple method of managing healthcare expenses.

Thus today, employers are searching for new benefits solutions that help attract and retain employees while also controlling healthcare expenses. The current generation of health spending accounts fails to meet these expectations for these aforementioned reasons.

SUMMARY OF THE INVENTION

To address these and other perceived shortcomings, one aspect of the present invention is directed to managing contributions to an accruable health spending account in an employer-sponsored plan offering a member an employer-funded defined contribution, at least one insurance premium option and the ability to specify an allocation of the defined contribution for payment of option premiums and, in turn, a directed contribution amount designated to such accruable account. Consistent with this aspect, the accruable account may be used to reimburse the member for qualified medical expenses, and the member may pay any premium shortfall using a tax-advantaged process such as a premium only payment plan. This aspect may be extended, for example, to processes for funding such an accruable account. This aspect may be implemented in server-client architecture, or in another general or specific purpose information processing system.

Another aspect of the invention is directed to presenting member-specific out-of-pocket expenses for a selected procedure offered by at least one health-care provider. Consistent with this aspect, calculation of such out-of-pocket expenses may take into account data corresponding to the specific member, such as lifetime-maximum data, yearly out-of-pocket maximum data, deductible data, copay data, and coinsurance data. Also, consistent with this aspect, out-of-pocket expenses may be calculated with reference to raw provider-supplied cost data or health plan data.

In yet another aspect of the present invention, alternative procedures may be highlighted upon request when appropriate in light of the procedure under scrutiny, benefits structure information including member-specific and health insurance data and costs.

BRIEF DESCRIPTION OF THE DRAWINGS

Additional aspects and advantages of this invention will become apparent from the following detailed description of embodiments thereof, which proceeds with reference to the accompanying drawings, to which:

FIG. 4 is a sample client display consistent with contribution processing described in the embodiment of FIG. 3;

FIGS. 9 and 10 are sample client displays illustrating selection of health procedures and comparative out-of-pocket expense processing in accordance with the embodiment shown in FIGS. 8A and 8B;

FIG. 12 is a sample client display indicating alternative procedures according to the embodiment shown in FIG. 11;

DETAILED DESCRIPTION OF THE EMBODIMENTS

Figure 1:
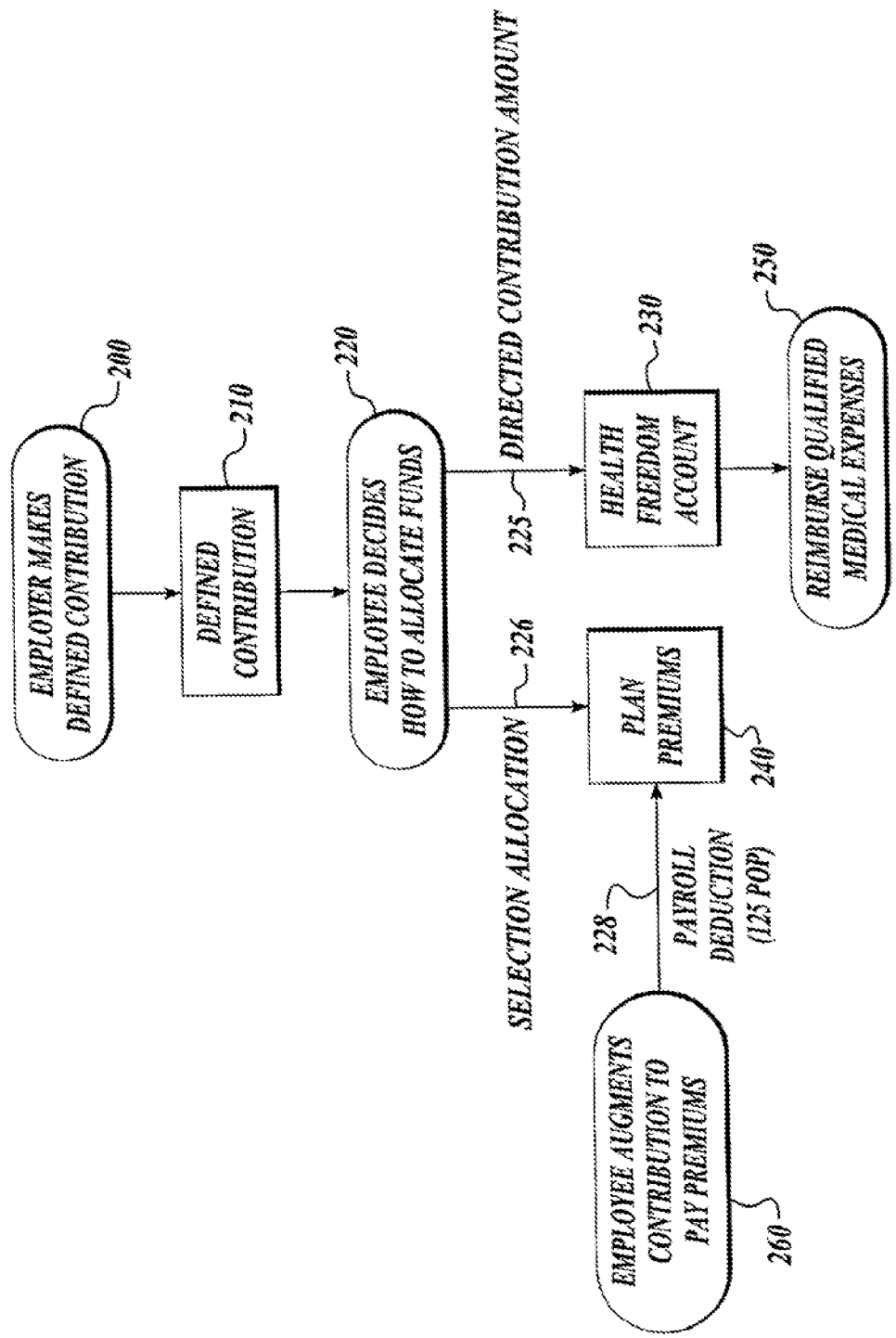
FIGS. 1 & 2 diagrammatically illustrate accruable health spending account establishment and management according to a first embodiment of the invention.

An accruable health spending account or health freedom account consistent with the disclosed embodiments of the invention is compliant with IRC §105. In particular, this accruable account (shown in FIG. 1 as accruable account 230) has the following characteristics: 1) it is presently contemplated to be funded exclusively using employer funds (though such funds can be controlled and allocated by the health plan member as will be discussed hereinbelow); 2) it is presently contemplated that withdrawals from the account can only be made against funds actually in existence in the account at the time of withdrawal; 3) such funds can be withdrawn only for the payment of submitted qualified medical expenses as defined in IRC §213; and 4) funds remain in the account whilst the corresponding health plan member remains eligible to participate in the plan which has the benefit of potentially being able to accumulate and roll-over funds from year to year (in stark contrast with conventional employee funded IRC §125 flexible spending accounts).

Accruability is believed an important component in controlling rising healthcare costs because it creates opportunity cost. With an accruable account, individuals will now have reason to ask the question, "Am I better off saving or consuming?" Enabling employees or health plan members to roll forward pre-tax dollars for reimbursement of qualified medical expenses would remove one of the most onerous restrictions of the current healthcare spending FSA, the inability to accrue unspent dollars from year to year. The ability to accrue money tax-free would dramatically increase the attractiveness of healthcare spending accounts.

Accruable health spending account establishment and management according to a first embodiment of the invention will now be described with reference to FIGS. 1 & 2. At the first stage, the employer offering a health plan chooses one or more health plans to offer employees/health plan members (FIG. 2 stage 300) and then develops and makes a defined contribution 210 in line with such offerings, the defined contribution having a sum certain or relative value as is known in the art (FIG. 2, stage 310 and FIG. 1, stages 200) from which the employee/health plan member may use to make informed health care choices. Then, the member will access the employer defined contribution information online (FIG. 2, state 320) and will allocate funds between health insurance premium option 240 and an employer-funded accruable health spending plan 230 created under IRC §105 (FIG. 1, state 220, FIG. 2, state 330) for that member.

More specifically, according to this embodiment, the member will select one or more insurance options offered by the employer, each option defining a discrete premium option having an associated option cost. The member will decide the premium option best fitting his/her circumstances (one or more premium option selections), and will decide how much of the employer's defined contribution will go towards paying the selected premium option 240, otherwise known as a selection allocation 226. Invariably, this selection allocation will be less than or equal to the total option cost for the selected insurance premium option(s).

Figure 2:
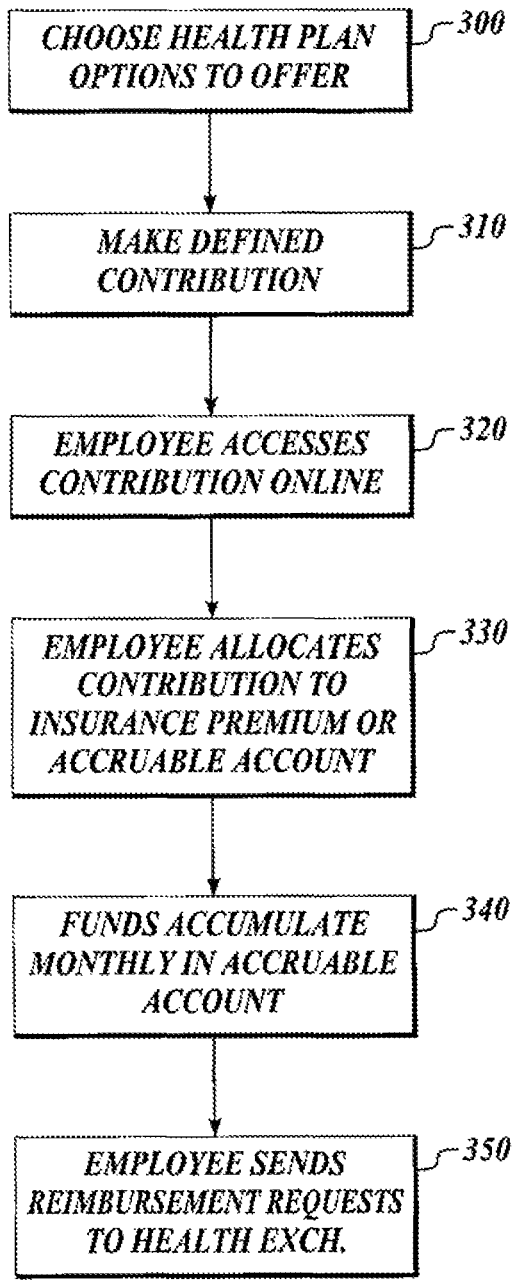

According to the embodiment shown in FIGS. 1 and 2, the remainder of the employer funds presented in the employer's defined contribution 210 (i.e. subtracting the selection allocation 226 from the defined contribution 210) will go to fund the accruable health spending account 230 as a directed contribution amount 225. Alternatively, although not shown in the Figs., the directed contribution amount 225 could be tied to the option cost, which give the member less flexibility and the employer more control over the accumulation rates in the accruable health spending account 230. In another embodiment, the employer need not actually maintain funded individual accruable accounts 230 but pool such accounts with employer funds as long as balances/credits and reimbursement debits can be maintained as is well known in the art. This technique simplifies account management responsibilities form employer while adding little delay to the contribution/reimbursement process.

In the embodiment presented in FIGS. 1 and 2, the directed contribution amount 225 accumulates monthly in the accruable health spending account 230 (FIG. 2, state 340). Note, here that the member need not equate the selection allocation 226 with the premium option cost and in fact may conveniently make up the difference using pre-tax employee funds (FIG. 1, state 260) using payroll deductions/transfers (aka member's out of pocket premium cost) 228 in accordance with IRC §125 premium only plan (POP) guidelines. This has the effect of boosting funds available to the member for qualified medical reimbursement on a rolling basis (as funds are present in the account, no use or lose requirements).

Under IRS Section 125, the law allows certain group insurance premiums to be paid with pre-tax dollars. By using a POP, dollars used to pay for the premium are deducted before taxes. This eliminates city, state, federal income tax, Social Security and Medicare taxes on those dollars. Thus members can save 20% to 40% compared to paying the premium using post-tax dollars. Employers save the matching Social Security and Medicare tax, and federal and state unemployment taxes, plus worker's compensation, depending on the state regulations. POP accounts may also be used to supplement the employer's defined contribution when the option cost for the selected option premium exceeds the defined contribution.

Once funds are available in the savings account 230, they may be used at the member's election to pay for QME expenses (FIG. 2, state 350, FIG. 1, state 250).

Figure 3:
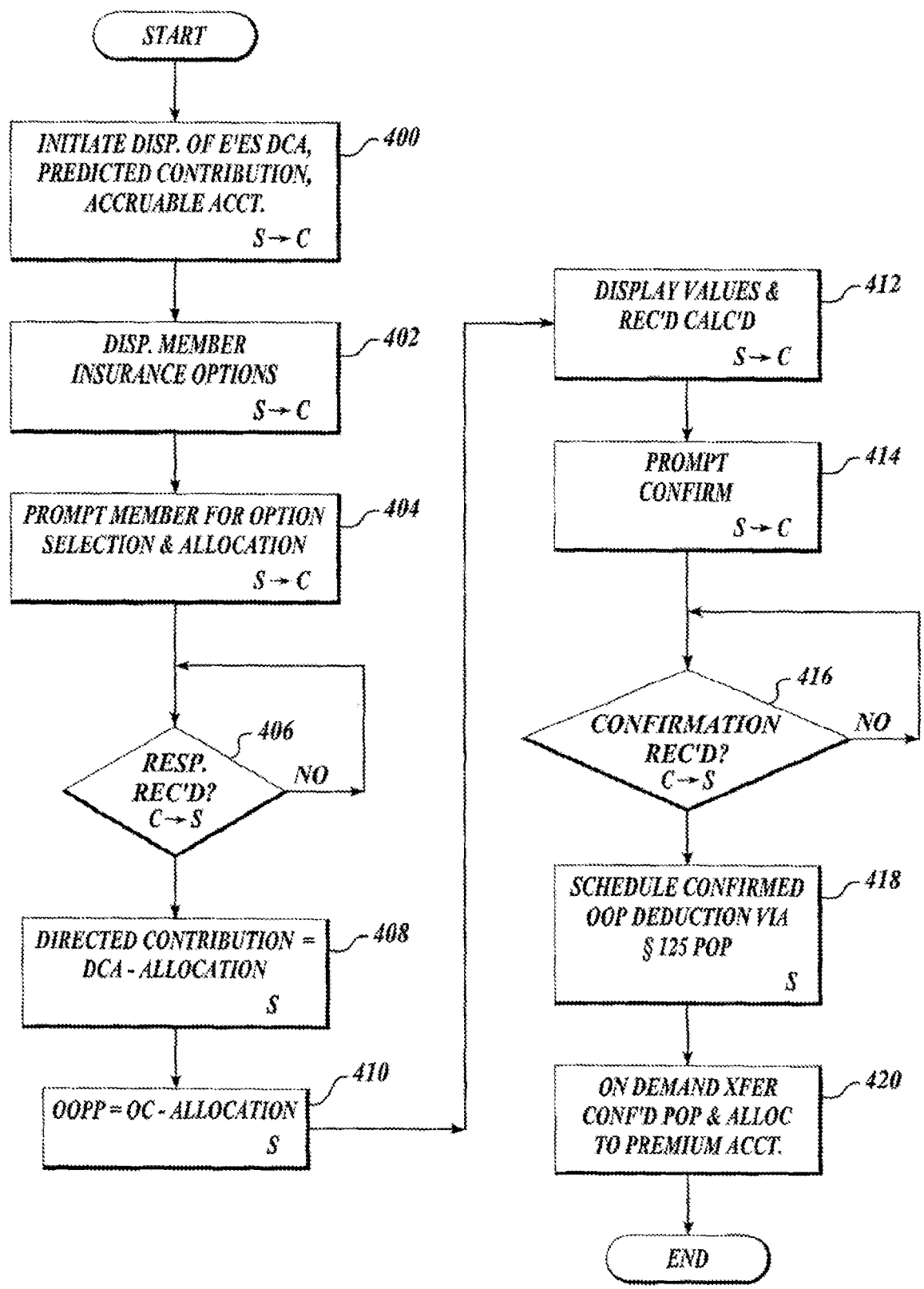
FIG. 3 is a flow chart detailing contribution processing of an accruable health spending account according to a second embodiment of the invention.
Figure 13:
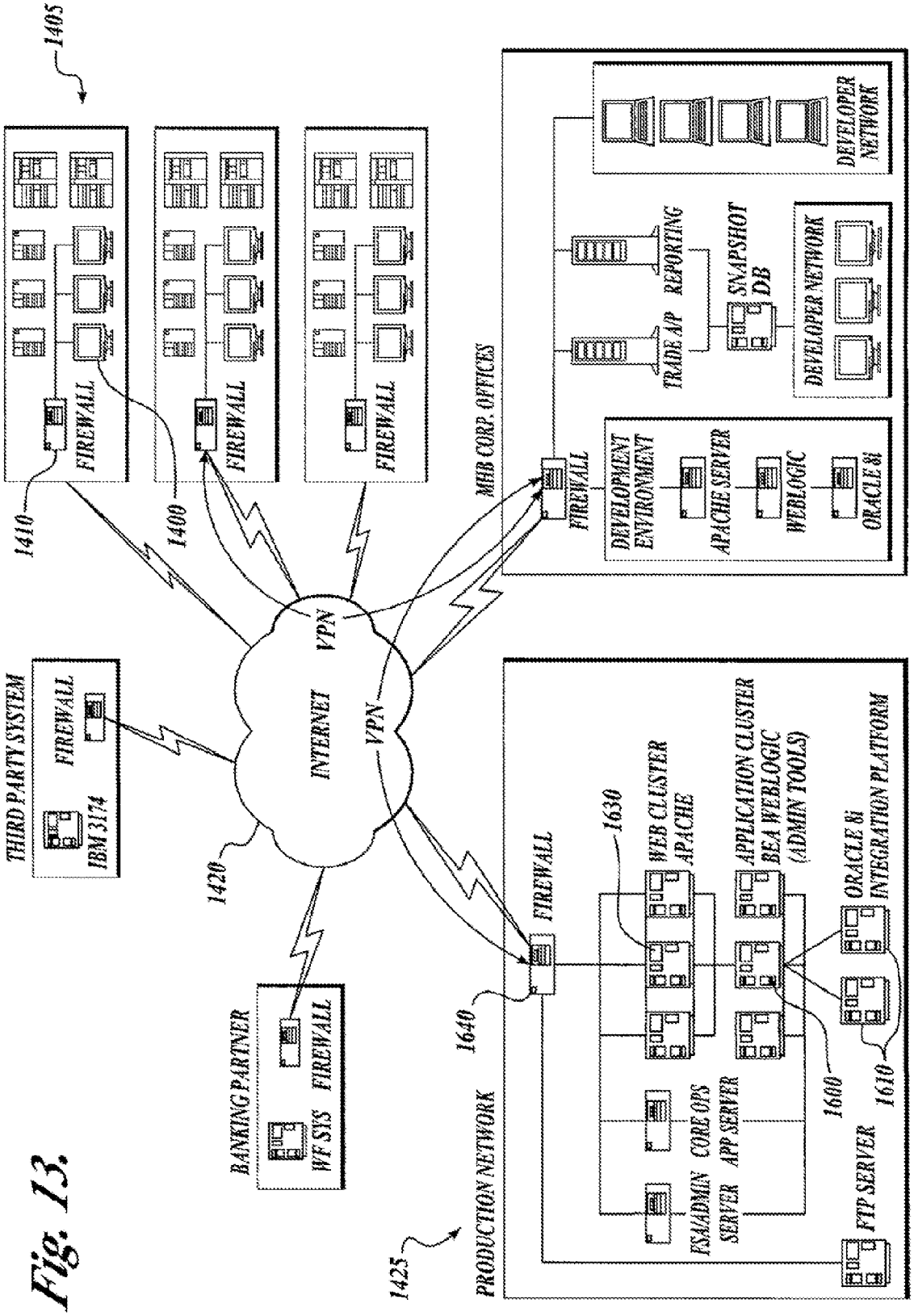
FIG. 13 is a representative client-server architecture consistent with the disclosed embodiments of the present invention.

Accruable health spending account contribution processing according to a second embodiment of the invention is deemed appropriate with reference to the flowchart of FIG. 3 and the sample display of claim 5. With reference to FIG. 3, health freedom account processing begins at step 400. At step 400 display of the employer-defined contribution amount and health freedom account status for the particular member is displayed to the user. This display initiation could emanate from a server command to a client in signal form as is well-known in the art (or could be performed locally to one information processing device). It should be realized in the flowchart of FIG. 3 as well as other flowcharts presented and described herein, the notation "S" stands for a server-oriented processing step consistent with client-server general purpose computing architecture (an example is shown and described herein with reference to FIGS. 13 and 14 e.g. client 1400 in communication with server 1600 via Apache web server 1630 coupled to firewall 1640 which then traverses the internet 1420 to firewall 1410 and LAN 1405), the notation "C" denotes a client oriented step, the notation "S→C" denotes messaging, signaling, command or instruction processing initiated by the server to the client device, and the notation "C→S" denotes messaging, signaling, command or instruction processing from the client device to the server.

Turning back to FIG. 3, the predicted contribution amount information calculated as to difference between the employer-defined contribution amount minus a given premium option cost, may be displayed as well to the member at step 400. Control thereafter passes to Step 402 in which display of one or more member insurance options as specified in the employer-defined contribution amount 210 and employer health plan documentation is initiated. Control thereafter passes to Step 404 in which is initiated for the member to make premium option selection and selection allocation 226 of the defined contribution amount 210 as described above. Thereafter, control passes to Step 406.

At Step 406 the information processing system awaits member input. Referring briefly to the sample client display of FIG. 4, Prompt 500, 502 and 506 provide an interface for the member according to the present embodiment to undertake or investigate certain insurance premium selection options according to the present embodiment. Further, Prompts 504 and 508 allow the member to undertake comparative or side by side evaluation of medical, dental and other insurance plan and premium alternatives.

Turning back to FIG. 3, once the selection and allocation information has been received from the member, control passes to Step 408 in which the directed contribution amount 225 on a given time period basis to the accruable health spending account is calculated as described above. Control thereafter passes to Step 410. At Step 410, the member's out-of-pocket premium cost 228 is calculated by subtracting the ascertained selection allocation 226 from the option cost received above with reference to Step 406. Control thereafter proceeds to Step 412 in which the display of the directed contribution amount 225, selection allocation 226 and the out-of-pocket premium cost 228 is presented to the member. These can be shown in summary form as depicted by summaries 530 and 532 illustrated in FIG. 4 based on differing premium option scenarios. Control thereafter passes to Step 414. In Step 414 confirmation from the member is prompted, the member's selections are confirmed at the client end at step 416. Control thereafter passes to Step 418. At Step 418 confirmed out-of-pocket premium costs presented to the member are scheduled for deduction from the member's pre-tax POP account or payroll deduction in accordance with Internal Revenue Code §125 as described above. Also, though not shown in the Figure, in the confirmed directed contribution amount 225 may be scheduled for periodic deduction from employer funds in accordance with Internal Revenue Code §105 (IRC §105) to the member's accruable health spending account. Control thereafter passes to Step 420 in which on demand, transfer of confirmed POP and confirmed selection allocation funds are transferred to the health insurer's premium account and paid according to U.S. Internal Revenue Code and specific health insurer directives, as is well known in the art. Processing thereafter terminates naturally.

Figure 4:
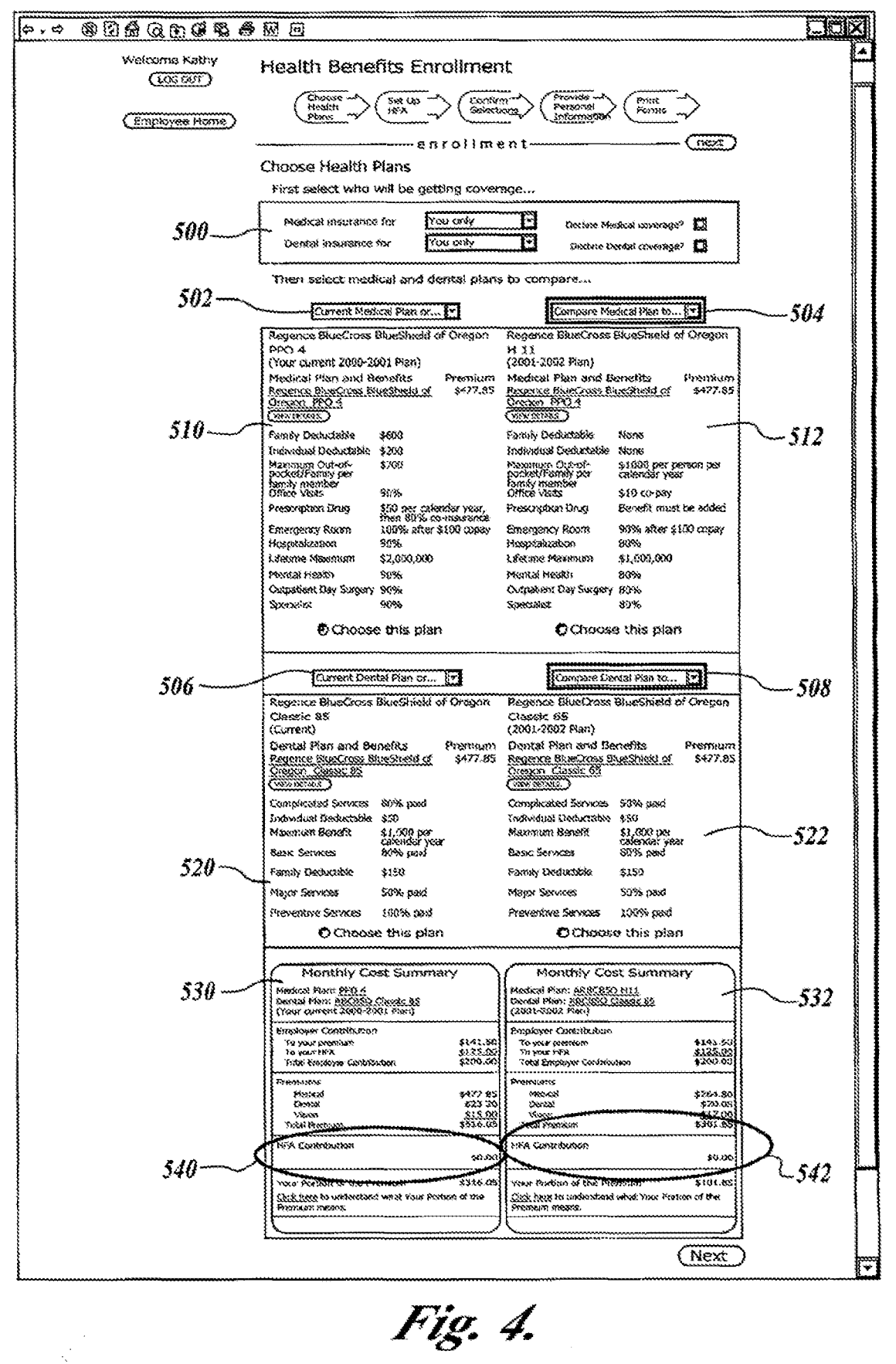

It should be realized that although current Internal Revenue Code regulations appear to prohibit employees or members from funding section 105 compliant accruable health spending accounts with their own money, it is certainly possible to include such capabilities and within the spirit of the present invention. For example, in FIG. 4, areas 540 and 542 of the screen include presentation of health freedom account contributions from the member himself or herself (herein zero because of current IRS regulations). It is contemplated that employee contributions to the health freedom account would be processed in a manner similar to how conventional flexible spending account contributions are made, with the exception that it is intended that the employee contributions would roll over and accrue from year to year just as the employer contributions currently do.

Figure 5:
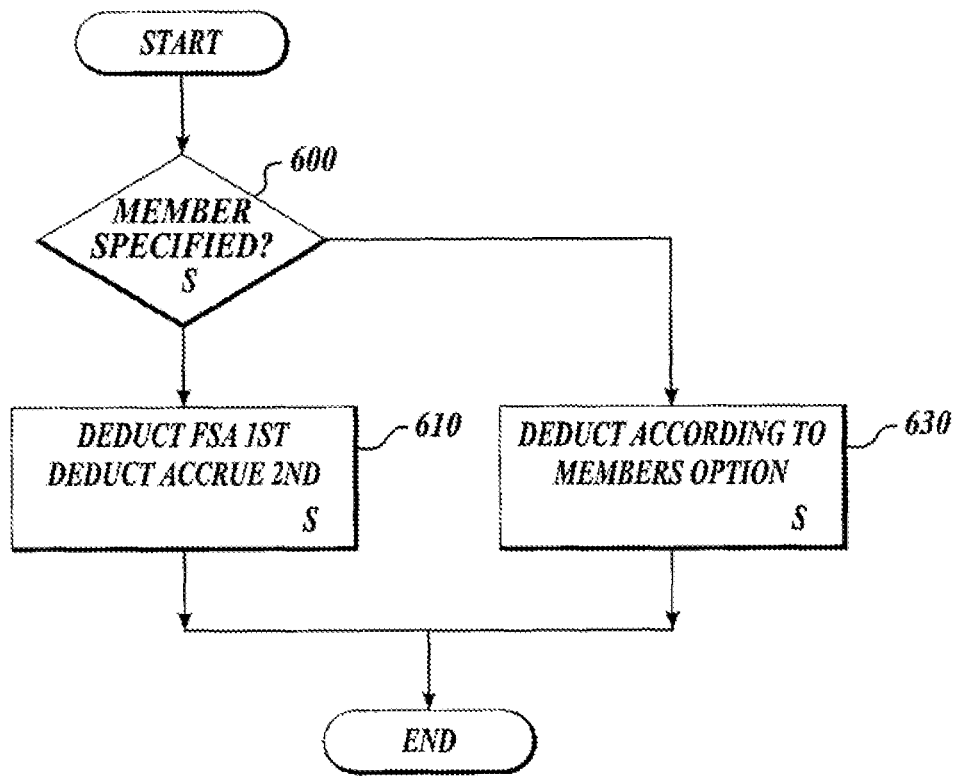
FIG. 5 is a flow chart illustrating qualified medical expense processing according to a third embodiment of the invention.

Qualified medical expense processing according to a third embodiment of the invention is deemed appropriate with respect to the accruable health spending account 230. With reference to FIG. 5, qualified medical expense processing according to the disclosed embodiments begins at Step 600. At Step 600, a determination is made whether a given member has specified non-default qualified medical expense processing. If so, control passes to Step 630. If not, control instead passes to Step 610, in which given qualified medical expense received is deducted from the member's flexible spending account first, and then deducted from the member's accruable account 230 second (once the FSA account has zeroed out for the year) as indicated in Step 620. Control thereafter terminates naturally.

If, however, in Step 610 a determination is made that the member has specified non-default processing for qualified medical expense information, as contained in benefit structure information associated with the member or otherwise, control instead passes to Step 630 in which deductions are made from the member's flexible spending account or health freedom account according to member specification. Processing thereafter terminates naturally as shown in FIG. 5.

Figure 6:
FIG. 6 is a sample client display consistent with qualified medical expense processing as described in the embodiment of FIG. 5.

It should be noted here that the above-described processing in FIG. 5 assumes conventional flexible spending account processing techniques including set aside maximum and deficit payment as is well-known in the art for FSA account. Under current IRS regulations, it is not contemplated that the accruable account 230 can be managed in a deficit mode, unlike flexible spending account, so funds can only be deducted to pay for qualified medical expenses in case of an accruable account 230 only when funds are on deposit to pay for such expenses either fully or partially. However, no technical reason exists for preventing this from occurring and could be implemented if the IRS rules change. FIG. 6, in particular the transaction record 700 shown there and illustrates how a client device may depict health freedom account transactions involving the deduction of qualified medical expenses as described above referenced to FIG. 5.

Figure 7:
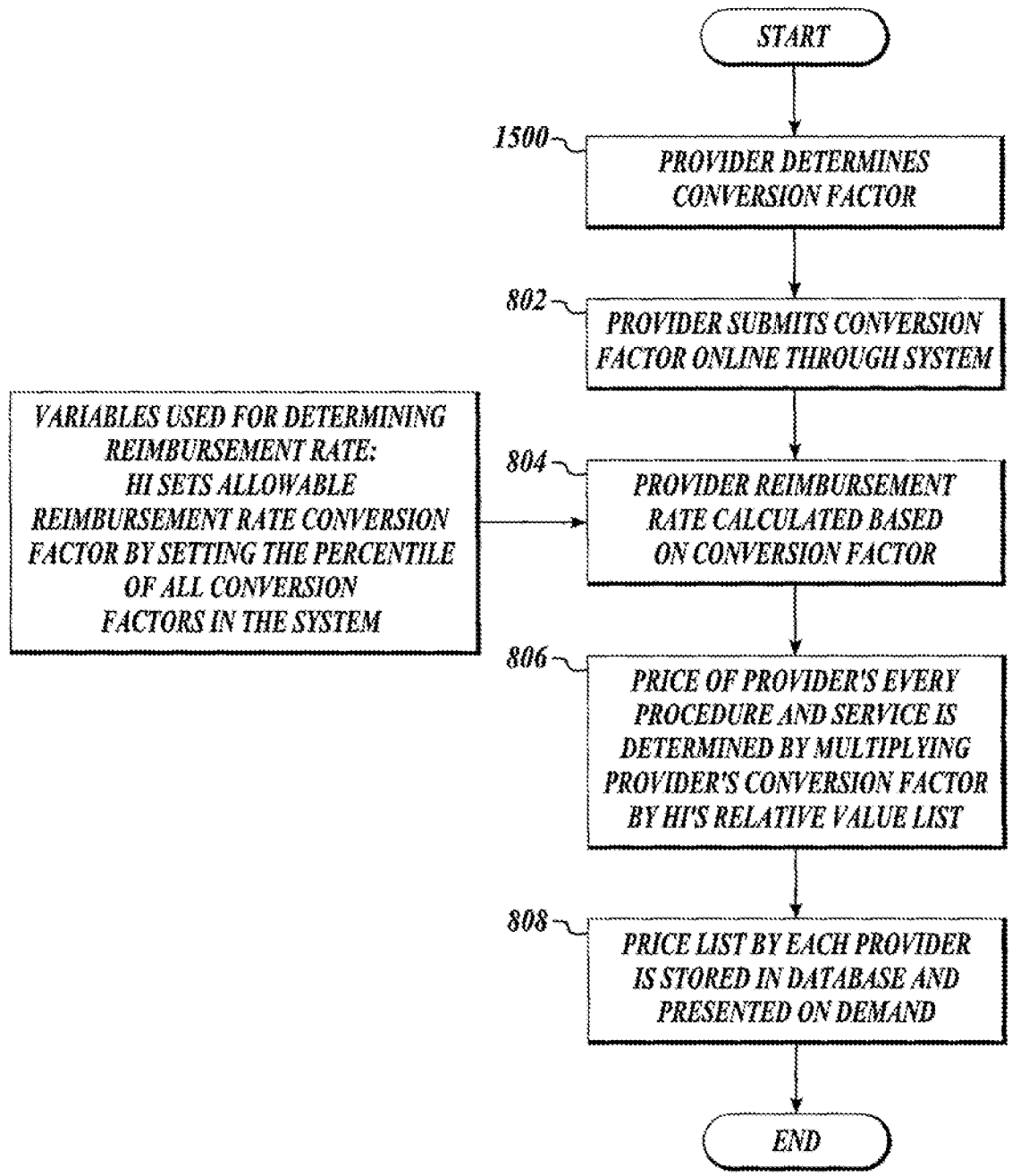
FIG. 7 is a flow chart depicting provider database information processing according to a fourth embodiment of the invention.

Provider costing information according to a fourth embodiment of the invention is now detailed with reference to FIG. 7. Processing begins at Step 800 where the provider determines his or her conversion factor to be applied against a predefined relative scale, such as the well-known Medicare relative value index. As will be appreciated, doing so essentially establishes pricing information for the procedures that the provider sets the conversion factors for. Processing thereafter passes to Step 802 in which the provider submits conversion factor information online for subsequent storage in a provider database. Control thereafter passes to Step 804 in which the particular provider's reimbursement rate calculated based on the conversion factor relative to the relative value index utilized by the health insurer. Pricing of the provider's procedure and service is thereafter determined in Step 806 by multiplying the provider's conversion factor by the health insurer's relative value list of interest. Control thereafter passes to Step 808 in which a price list for the provider is generated in the provider information data base and presented on demand to members, health insurers, employers and other interested parties. Thereafter, provider cost processing according to this embodiment terminates naturally.

The Allowable Reimbursement Rate Conversion Factor is determined by setting the Allowable Reimbursement Rate Conversion Factor at a percentile of the conversion factors in the provider database. In the example in the FIG. 1, the Allowable Reimbursement Rate Conversion Factor is set at the 70th percentile of the conversion factors in the database, but it could be set at any level.

When a member searches for the price of a particular service or good, the health exchange system calculates the member's exact out-of-pocket price by reconciling the following variables:
  a. Provider's conversion factor multiplied by the value unit of the service.
  b. the value unit is a standardized value scale that compares the value of all goods and services relative to each other. For example, one value unit scale that could be used could be the 2001 Relative Value Unit scale from Medicare. However, other relative value scales could be used.
  c. The conversion factor multiplied by the value unit gives the price that that particular provider is changing for that service.
  d. The Allowable Reimbursement Rate Conversion Factor may be above or below that the conversion factor of that particular provider/supplier.
  e. If the provider's conversion factor is below the Allowable Reimbursement Rate Conversion Factor, then the payor will reimburse the provider/supplier for the full amount of the change, minus the member's obligation. The member's obligation is determined by the following variables:
    1. Member co-insurance
    2. Member out-of-pocket yearly maximum and stop loss and where the member is in relationship to the stop-loss limit at the time the services are rendered.
    3. Member deductible and where the member is in relationship to the deductible at the time the services are rendered.
    4. Other benefit structure limits, restrictions or variables.

Figure 8A:
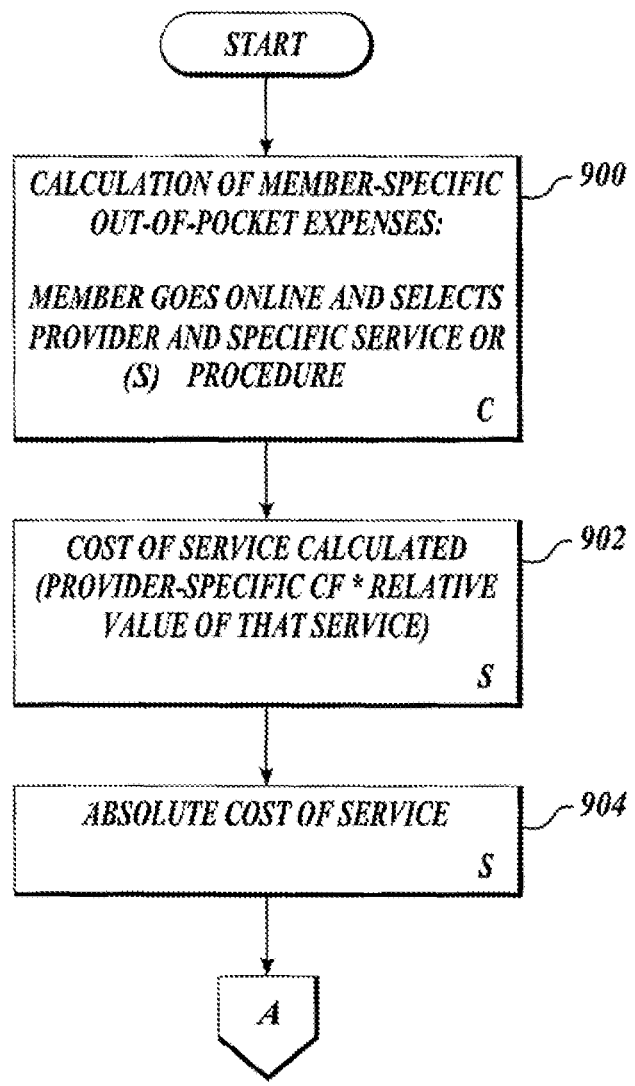
FIGS. 8a and 8b together are a flow chart describing out-of-pocket expense processing according to a fifth embodiment of the invention.

Member-specific out-of-pocket expense calculation according to a fifth embodiment of the invention is now detailed with reference to FIGS. 8A and 8B. Processing begins at Step 900 (FIG. 8A), in which the health plan member goes on line and selects provider's specific services or procedures as depicted in FIG. 9 and at the top of FIG. 10. Thereafter in Steps 902 and 904, the raw costs of services calculated for the specific providers and type of service or procedure desired prior to factoring in insurance benefits or spending account or reimbursement account processing. This is also typically considered as the absolute cost of service or the gross cost of service.

Figure 8B:
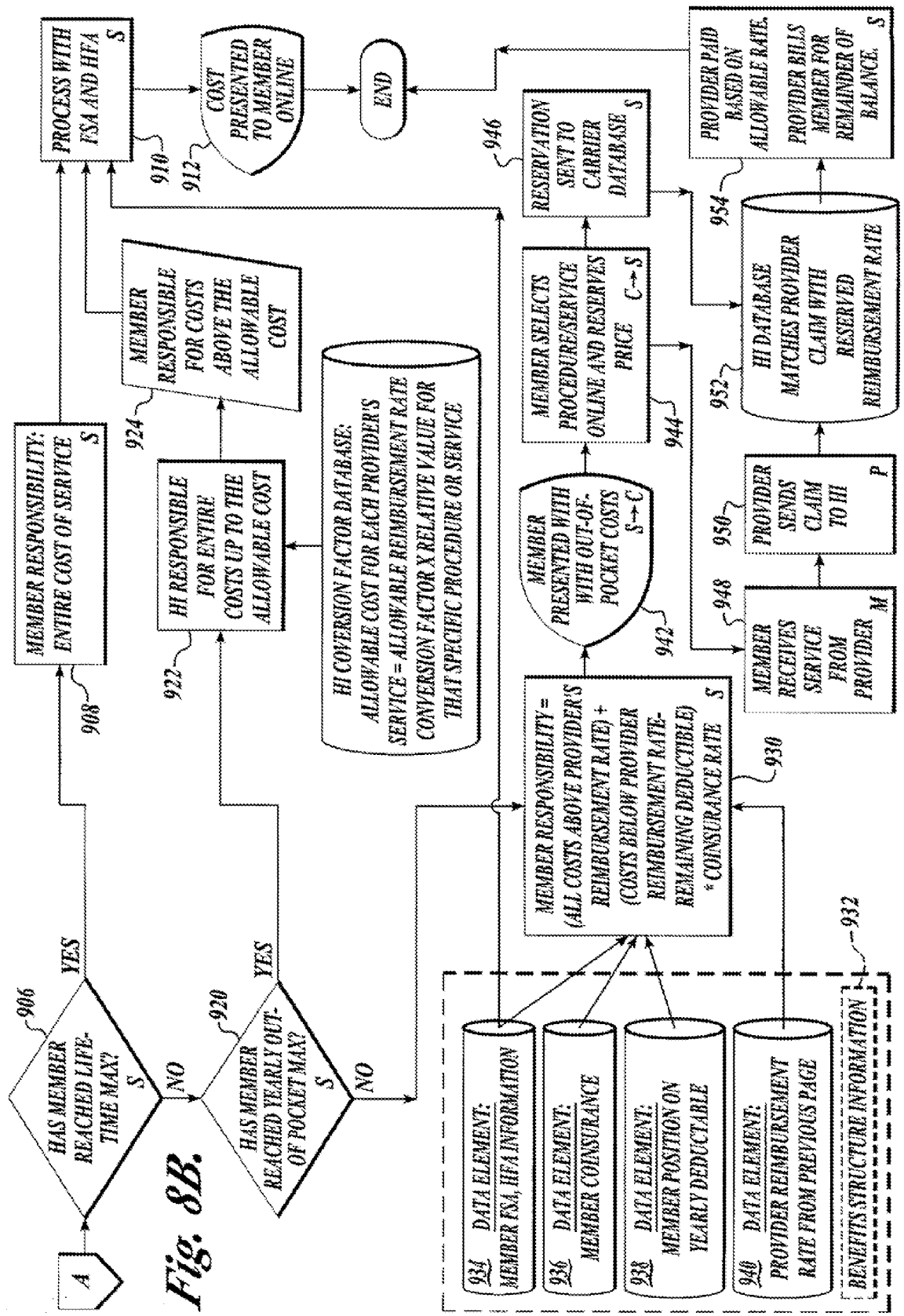
Figure 9:

Turning now to FIG. 8B, processing transitions to Step 906 in which a determination is made whether the members receive their life time maximum benefits under their health plan. This information is gathered by looking at the benefits structure information data base 932. If in Step 906, a determination is made that the lifetime maximum has been achieved, control passes to Step 908 in which the member's responsibility is determined to be the entire raw cost of service. Note, however, that the negotiated or reimbursable cost could be an alternative result based on the benefits structure information and/or health insurer information, and in particular, the type of cost constraints placed on the service provider. Control thereafter passes to Step 910 in which if the cost of service is perceived as a qualified medical expense under IRC Section 213, the cost of service is evaluated with reference to the available amount in the accruable account 230 and/or the member's flexible spending account with predence processing as discussed above with reference to FIG. 5. Control thereafter passes to Step 912 in which the true out-of-pocket costs (normalized to account for available FSA or accruable account funds) are presented to the member on line and control thereafter terminated naturally.

If, however, in Step 906 the determination is made that the member has not reached the life time maximum wall, control instead passes to Step 920. In Step 920, a determination is made whether the member has reached the yearly out-of-pocket maximum stop loss as defined in the benefits structure information for that specific member. If so, control passes to Step 922 in which the health insurer is determined to be responsible for the entire cost up to the allowable reimbursement rate set by the health insurer in negotiation with the provider. Thereafter in Step 924 a calculation is made of the out-of-pocket expense the member will be responsible for by subtracting the entire reimbursable allowable cost (obtained with reference to the health insurer allowable reimbursement rate as contained in the health insurer database 926) from the entire cost of service. Processing thereafter transitions to Step 910 in which the member's flexible savings account and health freedom account are reconciled with the remaining cost over the reimbursable allowance, and Step 912 the out-of-pocket pre-FSA and health freedom account application and post FSA and/or HFA allocation represented to the member on line. Processing thereafter terminates naturally.

If, however, in Step 920 a determination is made that the member has not yet reached the out-of-pocket maximum, control instead passes to Step 930. In Step 930 calculation is made as to what's the member's out-of-pocket responsibility is, herein equal to all costs exceeding the provider's reimbursement rate 940 as determined herein plus (costs below the provider's reimbursement rate—the remaining deductible from database 938 of the benefits structure information) multiplied by the co-insurance rate 936 (also contained in benefits structure information 932. Member specific FSA and accruable account 230 information 934 (again a part of the member-specific information residing in the aforementioned benefits structure information 932). Control thereafter passes to Step 931 in which realization of the member's out-of-pocket costs is made with respect to the variable amounts in the member's flexible spending account and/or health freedom account are reconciled. Control thereafter passes to Step 942 in which the member is presented with out-of-pocket costs both pre and post application of FSA and accruable account processing as described above. Control thereafter passes to Step 944 where the member may optionally select the procedure and service on line and pricing information. That reservation is stored in health insurance data base 952.

The member may lock in a conversion factor ahead of the time services are rendered by contacting the payor through the Internet or other electronic process. Rates for various products and services will be locked in for a specified time. For example, office visits and office-based procedures could be locked in for 12 weeks, while rates for inpatient and outpatient procedures could be locked in for a different period, say 16 weeks.

Providers/suppliers must accept locked-in rates as the full rate the provider may charge the member.

Thereafter, in this embodiment, it is contemplated processing will continue once the member receives service from the provider in Step 948. Of course, the provider sends the claim after service is rendered to the health insurer and indemnifying the member in Step 950 and thereafter in Step 954 the provider is paid based on the allowable rate and if there is any reservation and price lock in that's calculated with reference to the health insurance data base 952. Simultaneously in Step 954 the provider bills the member for the remainder of the balance and standard collection techniques for collection are employed in order to zero-out the balance. Out-of-pocket costs processing according to the present embodiment thereafter terminates naturally.

FIG. 10 shows a sample display of a comparison of different service providers consistent with out-of-pocket expense calculation described above with reference to FIGS. 8A and 8B. In this embodiment two potential service providers are listed on row 1180 of the Fig. Raw cost information as determined above with reference to Steps 902 and 904 and FIG. 8A, are presented on row 1100. Demographics as well as provider supplied information such as credentials and background are shown on rows 1120 and 1130, respectively. Subjective reviews from other members can be recorded, collected and presented as shown on comparative row 1140. Other information such as web site info (row 1170), independent ratings (row 1160) and public record information such as prior licensing and disciplinary actions (row 1150) can also be shown as is illustrated in FIG. 10.

Still referring to FIG. 10, the member's calculated out-of-pocket expenses as described above with reference to FIGS. 8A and 8B can be conveniently displayed in a comparative side-by-side format as shown in Row 1100 for the two service providers. In this example because of raw provider pricing differences and differences in provider participation with the health insurer, the out-of-pocket costs that the member receives with respect to one service provider is different that what he or she may receive with respect to another service provider. So that is detailed here with reference to Row 1110 in consideration of the raw costs presented on row 1100. Any number of ways of presenting costs differences or other graphic or tabular form may be utilized to present to the member out-of-pocket cost options available to him or her as they select a service provider in service.

Still referring to FIGS. 9 and 10, consider the following example:

Mr. Smith wants to get an initial cardiology evaluation. Mr. Smith has a benefit structure of 80% co-insurance, meaning that his insurance covers 80% of the charges of the service up to the Allowable Reimbursement Rate Conversion Factor. Mr. Smith has not reached his yearly out-of-pocket maximum, Mr. Smith has no deductible with this plan.

Mr. Smith uses the engine to search for an initial cardiology examination (FIG. 9).

Today the Allowable Reimbursement Rate Conversion Factor for cardiologists in this area is set at $50. The relative value unit for Initial Cardiology Evaluation is 10.

Thus the payor will reimburse a cardiologist up to a level of $500 for an initial cardiology visit. Dr. Wumps has set his conversion factor at $40. Thus, when Mr. Smith looks up Dr. Wumps, he sees that an initial cardiology evaluation through Dr. Wumps will be priced at $40×10=$400.

Mr. Smith's out-of-pocket obligation is personalized for his specific benefit plan: since Mr. Smith has an 80% co-insurance plan, Mr. Smith is responsible for 20% of the bill=$80.

Dr. Carson has set her conversion factor at $60. Thus, when Mr. Smith looks up Dr. Carson, he sees that an initial cardiology evaluation through Dr. Carson will be priced at $60×10=$600

Mr. Smith's out-of-pocket obligation is personalized for his specific benefit plan; since Mr. Smith has an 80% co-insurance plan, Mr. Smith is responsible for 20% of the bill up to the Allowable Reimbursement Rate of $500. Charges above the Allowable Reimbursement Rate are Mr. Smith's full responsibility. So, when Mr. Smith examines his obligation for having an initial cardiology visit with Dr. Carson, he sees that his out-of-pocket expense will be (20%×$500)+(the full difference between $500 and Dr. Carson's charge of $600)=$200

By requesting an initial cardiology evaluation, all providers providing this service will be presented to Mr. Smith based on the parameters Mr. Smith enters (for example: gender, location, price availability).

Figure 11:
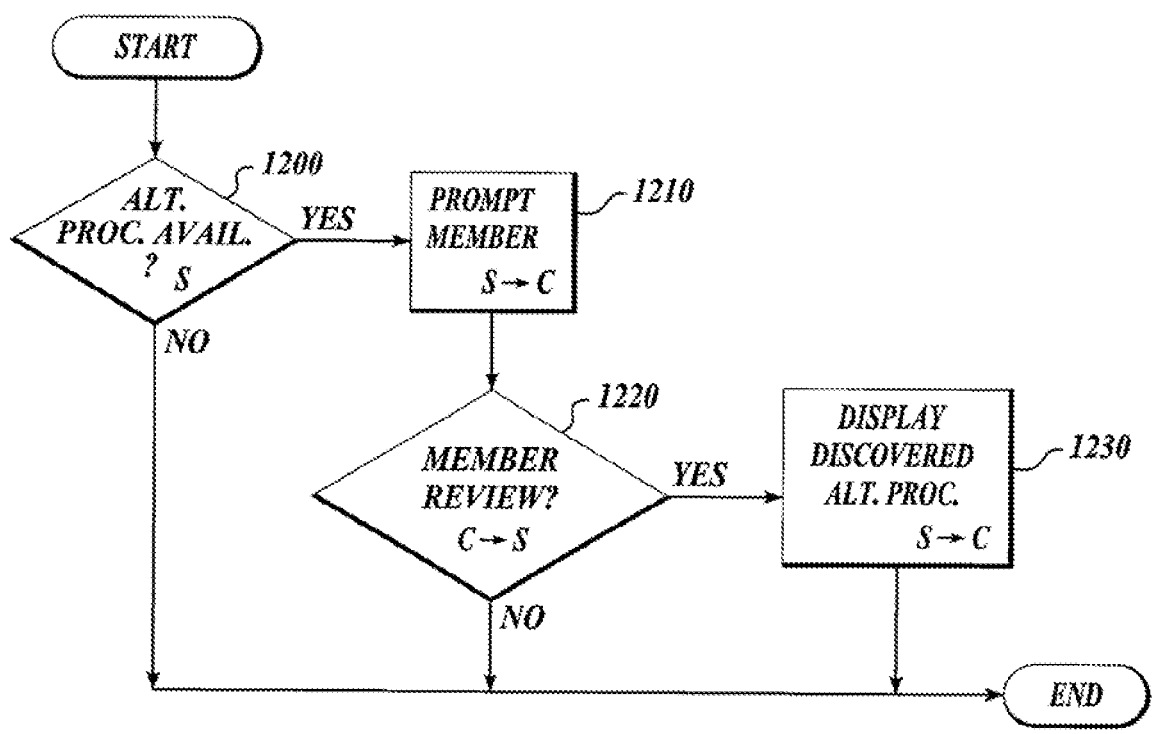
FIG. 11 is a flow chart depicting alternative procedure processing according to a sixth embodiment of the invention.
Figure 12:
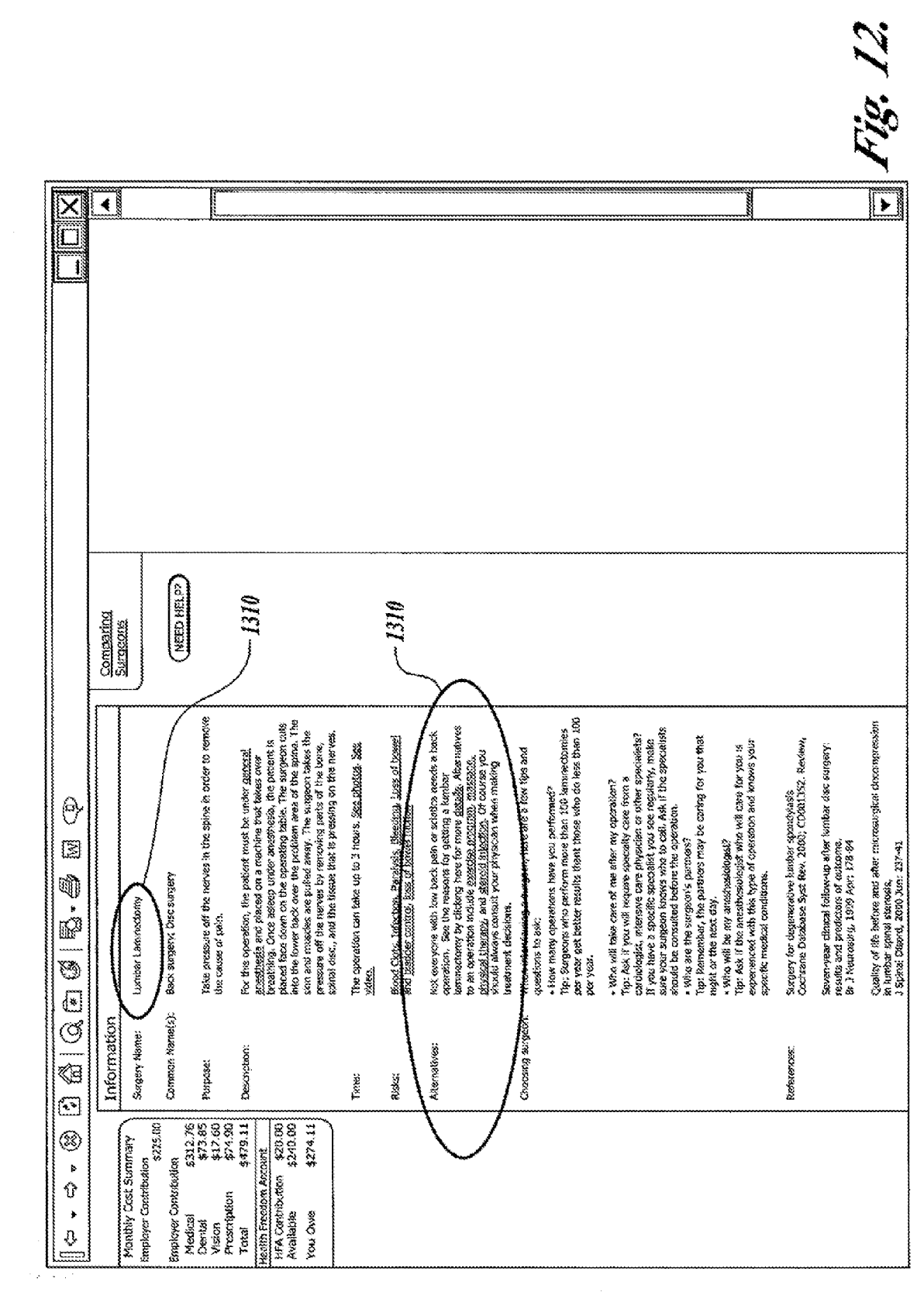

Alternative health care procedure processing according to a sixth embodiment of the invention is now detailed with reference to the flowchart of FIG. 11 and the screen display shot of FIG. 12. Turning first to FIG. 11, processing initiates at step 1200, in which a determination is made whether one or more alternative procedures to a selected health care procedure is available. This determination is made consulting member-specific data presented in the benefits structure information (e.g. what second opinion or alternative procedures are recommended by the member's health insurer) medical rights, comparison of the member-specific cost information (including raw and pre/post reimbursement account out-of-pocket costs calculated in accordance with processing described herein with reference to FIGS. 8A and 8B). After such inquiry is made, if no suitable processing is available, alternative health care procedure of this embodiment processing terminates naturally.

If, however, it is determined in step 1200 that alternative procedures do exist, processing instead transitions to step 1210 wherein the member is prompted whether they are interested in reviewing alternative procedures. If not, processing terminates naturally and discovered health care procedure information discovered in step 1200 is discarded.

If, however, in step 1210 a determination is made that the member does want to review alternative procedures available to the member, processing instead transitions to step 1230, in which the alternatives are presented to the user. FIG. 12 provides an example alternative procedure notification screen (herein visually displayed on a client screen associated with the member) consistent with the present embodiment including presentation of the selected procedure 1310 with alternative procedures 1310.

Figure 15:
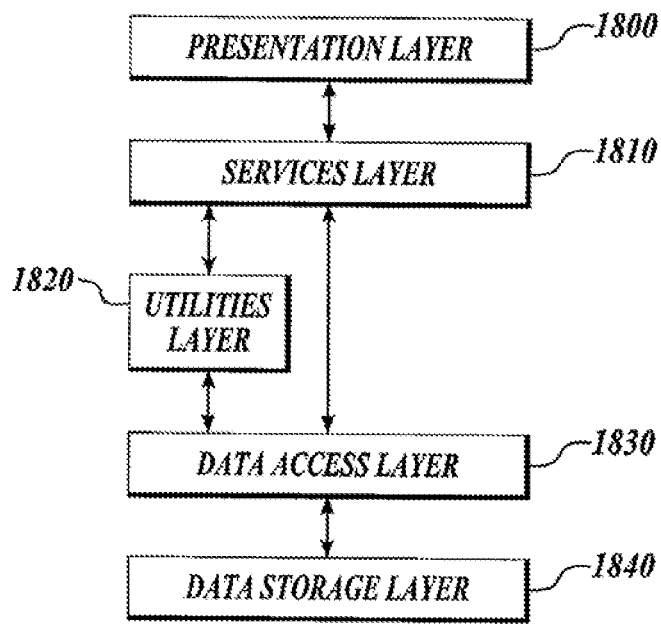
FIG. 15 is a software architecture diagram consistent with the disclosed embodiments of the invention.

The general health exchange system software architecture consistent with the above-described embodiments of the invention reflects a general n-tier web system architecture based principally on the Java 2 Enterprise Environment (J2EE) available from Sun Microsystems of Palo Alto, Calif. and Oracle database technologies available through the Oracle Corporation of Redwood City, Calif. The system is conceptually divided into a set of layered subsystems, as depicted in FIG. 15.

Data Storage Layer 1840—this layer provides persistent storage of data for the health exchange system. Data may be created and modified by the system, or it may be imported from external sources (for example, a physician directory).

Data Access Layer 1830—this layer provides an object-oriented abstraction to the higher layers, and insulates them from details of the underlying data storage machinery. It also enforces data consistency and access control.

Utilities Layer 1820—this layer provides shared components which can be used by multiple services, where there are common requirements. An example might be a pricing engine, which takes into account employee census characteristics, plan features, etc. and computes prices. Some utilities in this layer will be identified a priori; others will emerge opportunistically during design as common needs are identified.

Services Layer 1810—this layer consists of components for implementing particular services of the site, where a service is a "mini-application" with its own state data, user interaction flow, and business rules. Examples of services are Member Enrollment and Employer Reporting. Each service accesses stored data through the data access layer, and may use components in the utilities layer as appropriate. The services layer 1810 includes implementation of external systems interfaces, such as for CRM, financial system, carrier systems, etc. Many services may have side-effects, such as the logging of transactions, triggering of other events, etc.

Presentation Layer 1800—this layer contains a component for every service, which performs the actual formatting of displayed data in the client browser (along with client-side JavaScript, form field handling, etc.). The distinction between this layer and the services layer is that layout and style information is restricted to the presentation layer, while application state and control reside in the services layer.

Figure 14:
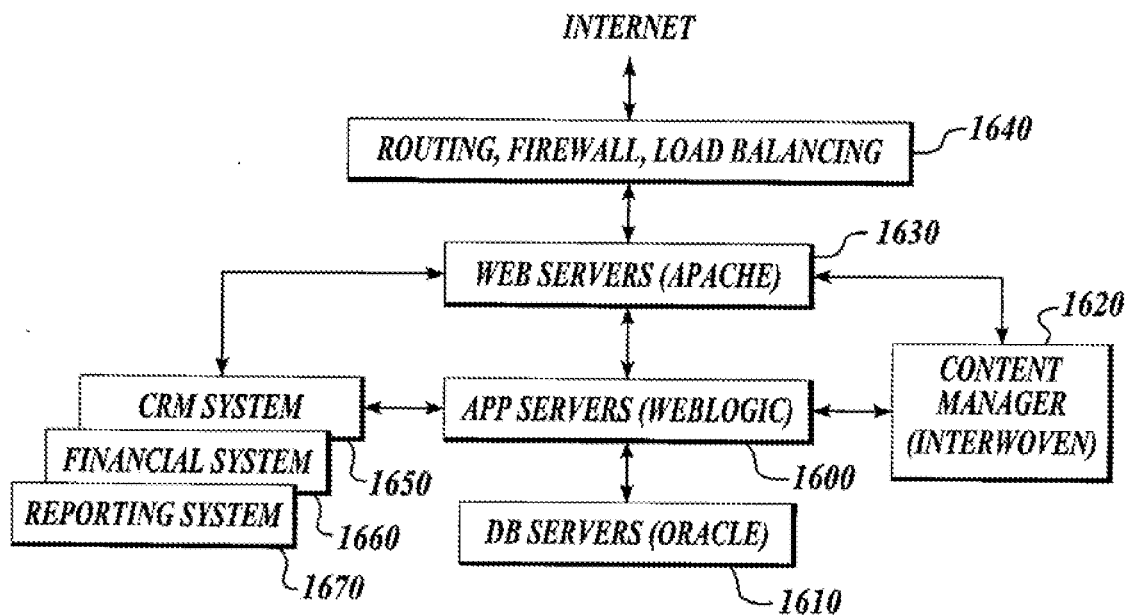
FIG. 14 is a functional system diagram consistent with the disclosed embodiments of the invention.

Discussion of the functional components of the health exchange consistent with the above-disclosed embodiments of the invention is deemed appropriate with reference to FIG. 14.

Application server tier 1600, based in part on BEA's WebLogic, provides a shrink-wrapped solution to many of the infrastructure issues that have slowed the development of distributed applications in the past. With the EJB component architecture, complex deployment issues such as transaction monitoring, fail-safe operation, security and scalability are handled at the server level, allowing developers to concentrate only on implementing the required business logic, including processing in accordance with the above-described embodiments. In addition, these servers can wrap Microsoft COM objects and automatically integrate them into its operating environment, opening access to a vast store of available software. The central component of this tier is one or more application servers responsible for implementing the Java Object architecture. WebLogic provides the ready-made infrastructure to support the rapid development and deployment of robust, secure and scalable server applications.

BEA's Object Request Broker (ORB) services resident on the application server tier 1600 allow access not only to remote data objects but also to remote software components, such as Javasoft's Enterprise Java Beans (EJB) or Microsoft's COM objects. Access to these remote components allows rapid integration of complex applications by capitalizing on the software development efforts of partner ASPs and on their specialized expertise. Common Object Request Broker Architecture (ORB) allows components to be distributed across disparate platforms, even if the objects are not written in the same programming language. CORBA management as well as other language specific ORBs are also built in to many of the leading J2EE application servers. Emerging XML standards and XML processing components as well as the emerging HL7 Version 3 CORBA-compliant health information exchange protocol make object-oriented data exchange among disparate systems a reality.

The health exchange system consistent with the above-described embodiments has adopted a Distributed 3-Tier IT Architecture (D3TA). Encapsulating business logic, including defined contribution amount processing, accruable health spending account contribution, reimbursement and management processing, member out-of-pocket expense processing, and alternative health care procedure processing as described above in an application tier permits: 1) taking advantage of readily available presentation layer applications such as web browsers and client-side GUI applications; 2) taking advantage of the Enterprise Java Bean (EJB) architecture to provide an off-the-shelf, robust and scalable middleware infrastructure; 3) take advantage of object-oriented design-methodology for rapid, high-quality development; 4) take advantage of Object Brokerage Architecture (ORB) for application integration with strategic partners and ASPs and to maximize code re-use; 5) take advantage of the Common Object Request Brokerage Architecture (CORBA) for data integration and language-independent access to remote objects and their methods.

BEA's Object Request Broker interfaces with the application objects through their respective CORBA (actually RMI over IIOP which allows for certain efficiencies in a pure Java environment while maintaining CORBA's language independence for interfacing to non-Java objects) interfaces. The ORB is responsible for establishing and managing the client-server relationships among the application objects. It is also responsible for locating and instantiating objects anywhere in the distributed environment in response to object request from the application.

Wrapper objects allow interfacing to non-CORBA based legacy applications and other non-CORBA ORB systems running either locally or remotely. By objectifying the legacy application API, one can seamlessly integrate these 2-tier applications into the D3TA while providing an easy migration path for future replacement of the legacy application. D3TA requires that all legacy applications be able to operate in client-server mode.

Enterprise Java Beans permits creation of the object model for the business logic and processing consistent with the above-described embodiments. Java technology can be further exploited by using the JDBC Data Access API for database connectivity. It allows the application server tier 1600 to access virtually any tabular data source from the Java programming language.

The Oracle 8I database platform makes up the data-server tier 1610 of the health exchange consistent with the disclosed embodiments of the invention. This tier is responsible for data storage and retrieval. From the application-server tier 1600, the data-server tier 1610 appears as a single data source with a unified data interface. Note again that data-objects can reside anywhere on the network and that wrapper objects can be used for interfacing with non-CORBA systems as is well known in the art. Most CORBA implementations allow for direct access to legacy RDBMs, providing pain-free data integration. Also, as is known in the art, technology now exists to bridge the gap that has existed in the past between the relational database world and the object oriented design world, allowing for the desirable separation between components and data while allowing relational database development to occur in the manner in which most DBA's are accustomed. TopLink for Java is an example of a production ready data encapsulation product.

Router tier 1640 and web server tier 1630, as well as third party tiers (CRM processing system 1650, Financial System 1660, and Reporting System 1670) and their functions, capabilities and responsibilities are well known in the art and can be implemented with well known programming techniques. Accordingly, further discussion of the same is omitted herein.

It will be obvious to those having skill in the art that many changes may be made to the details of the above-described embodiments of this invention without departing from the underlying principles thereof. The scope of the present invention should, therefore, be determined only by the following claims.

The invention claimed is:

1. A method of funding an accruable account for a member of an employer-sponsored health plan, the method comprising:
    determining by a pricing engine a directed contribution amount in accordance with a process comprising:
        presenting to the member via a web interface an employer-funded defined contribution having a value for a given time period;
        presenting to the member via a web interface at least one insurance premium option, the at least one insurance premium option defining an option cost for the given time period;
        receiving from the member at the pricing engine a premium option selection based on the at least one insurance premium option, the premium option selection including a selection allocation less than or equal to the option cost; and
        calculating at the pricing engine the directed contribution amount to the accruable account by subtracting either the selection allocation or the option cost from the defined contribution value; and
    transferring a first amount from an employer funded account to the accruable account, the first amount substantially equivalent to the directed contribution amount.

2. The method of claim 1, wherein the given time period comprises at least one of a group consisting essentially of a day, a week, a month, and a year.

3. The method of claim 2, wherein the defined contribution value, the selection allocation, the option cost, and the directed contribution amount are expressed in one or more units of currency.

4. The method of claim 1, further comprising presenting to the member via a web interface a predicted contribution amount for the accruable account, the predicted contribution amount based on either the defined contribution value or the option cost.

5. The method of claim 4, further comprising: calculating by the pricing engine a predicted contribution amount for the accruable account by subtracting the option cost from the defined contribution value.

6. The method of claim 1, further comprising: calculating by the pricing engine an out-of-pocket premium cost for the premium option selection by subtracting the selection allocation from the option cost.

7. The method of claim 1, further comprising: withdrawing a first sum from a member's flexible spending account to reimburse the member for a medical expense; and
    withdrawing a second sum from the accruable account to reimburse the member for a remainder of the medical expense when the first sum is less than the medical expense.

8. A method of providing to a member an employer-sponsored health plan and an accruable account for paying health-related expenses, the method comprising:
    presenting to the member via a web interface multiple insurance options for a given time period;
    receiving from the member at a server an insurance option selection from the multiple insurance options;
    establishing by the server the accruable account for the member;
    instructing by the server that a first amount from an employer funded account be transferred to the accruable account, the first amount substantially equivalent to a contribution amount by the employer to the accruable account; and
    transferring a sum from the accruable account to the member for a qualified medical expense.

9. The method of claim 8, wherein presenting the multiple insurance options includes presenting a cost of each of the multiple insurance options for the given time period to the member.

10. The method of claim 8, further comprising: calculating an out-of-pocket premium cost for the insurance option selection and presenting the out-of-pocket premium cost for the insurance option selection to the member.

11. The method of claim 8, wherein the accruable account is associated with a pooled fund and is not individually funded.

12. The method of claim 8, wherein transferring the sum from the accruable account further comprises:
    transferring the sum from the accruable account to reimburse the member for the qualified medical expense during the current year; and
    transferring another sum from the accruable account to reimburse the member for another qualified medical expense during the subsequent year,
    wherein the another sum comprises at least a portion of an unused balance from the current year in the accruable account.

13. The method of claim 8, wherein the accruable account is funded only by the employer.

14. The method of claim 8, further comprising:
    upon the member moving to a new employer, establishing a new accruable account associated with the new employer for the benefit of the member; and
    transferring any unused balance in the accruable account to the new accruable account.

15. A method of managing an employee's health care spending by an employer, the method comprising:
    establishing via a multiple party client-server computing architecture an accruable account for paying health-related expenses of the employee;
    reimbursing the employee via the multiple party client-server computing architecture for one or more qualified medical expenses incurred during a first year by debiting the accruable account; and
    carrying forward any unused balance in the accruable account for qualified medical expenses incurred during a subsequent year by the employee.

16. The method of claim 15, wherein the accruable account is funded only by the employer.

17. A method of paying out-of-pocket health care expenses for a member of an employer-sponsored health plan, the method comprising:
    enrolling the member in an employer-sponsored health plan via a multiple party client-server computing architecture;
    establishing an accruable account for the member via the multiple party client-server computing architecture;
    establishing a flexible spending account for the member via the multiple party client-server computing architecture;

determining by a pricing engine of the multiple party client-server computing architecture a directed contribution amount to be paid by the employer to the accruable account;

transferring by the multiple party client-server computing architecture a first amount from an employer-funded account to the accruable account;

withdrawing by the multiple party client-server computing architecture a first sum from the flexible spending account to reimburse the member for a medical expense;

withdrawing by the multiple party client-server computing architecture a second sum from the accruable account to reimburse the member for a remainder of the medical expense when the first sum is less than the medical expense; and carrying forward by the multiple party client-server computing architecture any unused balance from a current year in the accruable health account for reimbursing the member for qualified medical expenses incurred during a subsequent year.

18. The method of claim 17, wherein the accruable account is funded only by the employer.

* * * * *